(12) United States Patent
Juni (10) Patent No.: US 7,310,407 B2
(45) Date of Patent: Dec. 18, 2007

(54) NUCLEAR MEDICAL IMAGING DEVICE

(76) Inventor: Jack E. Juni, 25595 York St., Royal Oak, MI (US) 48067

(*) Notice: Subject to any disclaimer, the term of this patent is extended or adjusted under 35 U.S.C. 154(b) by 0 days.

(21) Appl. No.: 11/218,936

(22) Filed: Sep. 2, 2005

(65) Prior Publication Data

US 2006/0050845 A1 Mar. 9, 2006

Related U.S. Application Data

(60) Provisional application No. 60/652,424, filed on Feb. 11, 2005, provisional application No. 60/607,319, filed on Sep. 3, 2004.

(51) Int. Cl.
*G21N 23/04* (2006.01)
*G01T 1/166* (2006.01)
*G21K 1/02* (2006.01)

(52) U.S. Cl. ............... 378/63; 250/363.05; 250/363.1; 250/394

(58) Field of Classification Search ............... 378/9, 378/63, 92, 124, 4–20, 62, 146–155, 189; 250/370.08–9, 363.04–5, 363.08, 363.1, 250/394–5, 586

See application file for complete search history.

(56) References Cited

U.S. PATENT DOCUMENTS

| | | | |
|---|---|---|---|
| 4,090,080 A | 5/1978 | Tosswill | |
| 4,229,651 A | 10/1980 | Danos | |
| 4,584,478 A | 4/1986 | Genna et al. | |
| 4,821,304 A | 4/1989 | Danos | |
| 4,937,453 A | 6/1990 | Nelson | |
| 5,021,667 A | 6/1991 | Genna et al. | |
| 5,032,728 A | 7/1991 | Chang et al. | |
| 5,165,410 A * | 11/1992 | Warne et al. | ............... 600/425 |
| 5,187,659 A * | 2/1993 | Eberhard et al. | ............... 378/9 |
| 5,225,980 A | 7/1993 | Hsieh et al. | |
| 5,600,144 A | 2/1997 | Worstell | |
| 5,600,145 A | 2/1997 | Plummer | |

(Continued)

FOREIGN PATENT DOCUMENTS

EP 0289737 A1 11/1988

OTHER PUBLICATIONS

M.M. Rogulski, H.B. Barber, H.H. Barrett, F.L. Shoemaker and J.M. Woolfenden, University of Arizona, Tucson, Arizona, "Ultra-High-Resolution Brain Spect Imaging: Simulation Results," IEEE Transactions on Nuclear Science, vol. 40, No. 4, Aug. 1993, pp. 1123-1129.

(Continued)

*Primary Examiner*—Edward J. Glick
*Assistant Examiner*—Anastasia S. Midkiff
(74) *Attorney, Agent, or Firm*—Gifford, Krass, Sprinkle, Anderson & Citkowski, P.C.

(57) ABSTRACT

An apparatus for imaging a field of view, according to an embodiment of the present invention, comprises an x-ray source positioned adjacent to the field of view, a source mask located between the x-ray source and the field of view having at least one source aperture defined therethrough, and an emission detector, such as a gamma camera, adjacent to the field of view. The apparatus may allow substantially concurrent x-ray imaging and gamma imaging of the field of view.

24 Claims, 6 Drawing Sheets

U.S. PATENT DOCUMENTS

| | | | |
|---|---|---|---|
| 5,608,221 A | 3/1997 | Bertelsen et al. | |
| 5,638,817 A | 6/1997 | Morgan et al. | |
| 5,821,541 A | 10/1998 | Tumer | |
| 5,825,031 A | 10/1998 | Wong et al. | |
| 5,838,009 A | 11/1998 | Plummer et al. | |
| 5,841,140 A | 11/1998 | Mc Croskey et al. | |
| 5,900,636 A * | 5/1999 | Nellemann et al. | 250/363.04 |
| 6,040,580 A | 3/2000 | Watson et al. | |
| 6,147,352 A | 11/2000 | Ashburn | |
| 6,252,938 B1 | 6/2001 | Tang | |
| 6,359,279 B1 | 3/2002 | Gagnon et al. | |
| 6,399,951 B1 * | 6/2002 | Paulus et al. | 250/370.13 |
| RE37,899 E * | 11/2002 | Grodzins et al. | 378/86 |
| 6,501,828 B1 * | 12/2002 | Popescu | 378/150 |
| 6,504,157 B2 | 1/2003 | Juhi | |
| 6,525,320 B1 | 2/2003 | Juni | |
| 6,552,349 B2 | 4/2003 | Gagnon et al. | |
| 6,649,914 B1 * | 11/2003 | Moorman et al. | 250/363.06 |
| 6,661,865 B1 | 12/2003 | Popilock | |
| 6,670,614 B1 * | 12/2003 | Plut et al. | 250/363.04 |
| 2001/0044574 A1 * | 11/2001 | Warne et al. | 600/407 |
| 2003/0026386 A1 | 2/2003 | Tang et al. | |
| 2003/0128813 A1 | 7/2003 | Appleby et al. | |
| 2003/0235272 A1 | 12/2003 | Appleby et al. | |
| 2004/0028181 A1 * | 2/2004 | Charles, Jr. et al. | 378/92 |
| 2004/0081272 A1 | 4/2004 | Chinju et al. | |
| 2004/0141586 A1 * | 7/2004 | Hsieh et al. | 378/63 |
| 2004/0156478 A1 | 8/2004 | Appleby et al. | |
| 2004/0251420 A1 * | 12/2004 | Sun | 250/370.09 |
| 2004/0264629 A1 * | 12/2004 | Tang | 378/7 |
| 2005/0001170 A1 * | 1/2005 | Juni | 250/363.04 |
| 2005/0194540 A1 * | 9/2005 | Fenster et al. | 250/363.05 |
| 2005/0207526 A1 * | 9/2005 | Altman | 378/20 |
| 2005/0207530 A1 * | 9/2005 | Inoue et al. | 378/63 |
| 2005/0213705 A1 * | 9/2005 | Hoffman | 378/63 |
| 2005/0226364 A1 * | 10/2005 | Bernard De Man et al. | 378/9 |
| 2006/0086905 A1 * | 4/2006 | Fritzler et al. | 250/363.05 |
| 2006/0093088 A1 * | 5/2006 | Sowerby et al. | 378/63 |
| 2006/0239398 A1 * | 10/2006 | McCroskey et al. | 378/37 |
| 2007/0085011 A1 * | 4/2007 | Ritter | 250/363.05 |

OTHER PUBLICATIONS

J.J. Williams, W.P. Snapp, G.F. Knoll, The University of Michigan, "Introducing SPRINT: A Single Photon Ring System for Emission Tomography," IEEE Transactions on Nuclear Science, vol. NS-26, No. 1, Feb. 1979, pp. 628-633.

W. Rogers, N. Clinthorne, J. Stamos, K. Koral, r. Mayans, G. Knoll, J. Juni, J. Keyes, Jr., B. Harkness, "Performance Evaluation of SPRINT, A Single Photon Ring Tomograph for Brain Imaging," J. Nucl. Med., vol. 25, No. 9, 1984, pp. 1013-1018.

W. Rogers, N. Clinthorne, J. Stamos, K. Koral, R. Mayans, J.Keyes, Jr., J. Williams, W. Snapp, G. Knoll, "SPRINT: A Stationary Detector Single Photon Ring Tomograph for Brain Imaging," IEEE Transactions on Medical Imaging, vol. MI-1, No. 1, Jul. 1982.

W. Rogers, N. Clinthorne, L. Shao, P. Chiao, Y. Ding, J. Stamos, K. Koral, "SPRINT II: A Second Generation Single Photon Ring Tomograph," IEEE Transactions on Medical Imaging, vol. 7, No. 4, Dec. 1988, pp. 291-297.

* cited by examiner

NUCLEAR MEDICAL IMAGING DEVICE

REFERENCE TO RELATED APPLICATIONS

This application claims priority of U.S. Provisional Patent Application Ser. No. 60/607,319, filed Sep. 3, 2004, and 60/652,424, filed Feb. 11, 2005, the entire content of both of which are incorporated herein by reference.

FIELD OF THE INVENTION

The present invention relates to generally to apparatus and methods of imaging, and in particular to medical imaging.

BACKGROUND OF THE INVENTION

Medical imaging devices take a variety of forms, including nuclear medical imaging devices such as described in Applicant's co-pending patent applications, the entire contents of which are incorporated herein by reference. As known to those of skill in the art, when using nuclear medical imaging devices, such as SPECT devices, it is desirable to determine the amount of radiation attenuation attributable to the portions of the subject surrounding the area being imaged.

SPECT (Single Photon Emission Computed Tomography) allows imaging of a subject by detecting gamma emissions from the subject. In medical imaging, a compound including a radioactive isotope is administered to a patient, the compound reaches a subject of interest, such as an organ, and gamma emissions are detected from the subject.

Gamma imaging techniques, such as SPECT, are emission imaging techniques, in which the distribution of an emissive material (such as a radionuclide) are of interest. In contrast, x-ray imaging of a subject, such as x-ray CAT scanning, is a transmissive imaging method that allows the attenuation properties of the subject to be determined. Emission images of a subject are also modified by the attenuation properties of the subject. Hence, it would be extremely valuable to obtain transmission and emission images of the subject together, so that the emission image can be corrected for the attenuation factors.

SPECT imaging of the heart or other organs is often complicated by the surrounding tissue absorbing or otherwise attenuating the radioactive emissions in a non-uniform manner, hindering the accurate reconstruction of an image. An x-ray or gamma ray CAT scan (often referred to as a transmission scan) can be performed along with SPECT (emission) imaging, and the CAT scan data used to determine the attenuation attributable to the patient's body. However, as conventionally performed, this approach presents a number of problems. First, current approaches to measurement of tissue attenuation require performing a transmission CAT scan (with either x-rays or gamma rays) either before or after the SPECT emission scan. The subject must remain absolutely motionless between these two scans in order that the attenuation measurements correlate with the emission images. Despite a subject's best efforts, movement of internal structures (e.g. colon contents) will occur, often over just minutes.

In addition, CAT scan apparatus are designed to operate quickly and at a high photon flux, so as to provide a "snapshot." SPECT imaging, on the other hand, is a low photon flux process that, by its nature, requires a much longer period in order to acquire enough data to form an image. As such, the patient's heart, lungs and other tissues move through a range of motion during the SPECT imaging session. This substantially reduces the correlation between the rapid CAT scan "snapshot" and the "time averaged" SPECT image.

Hence, it would be advantageous to collect the x-ray transmission signal and SPECT emission signals over a concurrent time span, so that subject motion has a similar effect on both the transmission and emission images. However, x-ray imaging is typically a faster process than SPECT imaging, and no previous apparatus has allowed concurrent x-ray and gamma imaging. Typically, an x-ray image is obtained quickly, then a gamma image is obtained relatively slowly, leading to serious problems in correlating the data.

In any case, interpretation of medical images can be problematic and it would be advantageous to have multiple images of a subject using different techniques, as long as the images can be readily and accurately interrelated. Hence, improved imaging techniques would be valuable, for example, to allow collection of improved imaging data, and more accurate diagnosis of patient problems.

SUMMARY OF THE INVENTION

Apparatus according to the present invention allows x-ray transmission imaging of a subject, such as x-ray CAT scanning, to be performed along with emission imaging such as gamma imaging. The x-ray imaging allows attenuation properties of the subject to be determined, and these can be used to correct emission imaging techniques, such as SPECT. Transmission and emission images of the subject can be obtained concurrently, so that the emission image can be accurately corrected for attenuation factors. X-ray imaging is typically performed with high x-ray flux levels, whereas gamma imaging typically is performed at much lower flux levels. However, x-ray transmission and emission images can be formed over similar imaging time spans, as measured from the start of image data collection to the end of image data collection, using a pulsed x-ray source with a low duty cycle (time on divided by time off). The duty cycle can be as low as 1%, or less, for example 0.1%. For example, an x-ray image can be reconstructed from scans or sections obtained during the shorter "on" times of the x-ray source, with the emission images built up during the longer "off" times. If emission imaging is not performed while the x-ray source is "on", this approach increases the emission imaging time by a factor related to duty cycle. However, as the duty cycle of the x-ray source is low, this factor may be insignificant.

An improved x-ray transmission imaging technique is also described, in which a plurality of x-ray sources, source apertures, and detector apertures are moved in coordinated manner so that x-ray beams remain in register through the source and detector apertures during a scanning process. This approach gives improved efficiency. Further, the use of narrow x-ray beams, which are substantially non-divergent over the field of view of the apparatus, reduces x-ray exposure of an imaged subject. A further advantage of non-divergent beams is increased resolution of the x-ray imaging. Low energy x-rays are typically scattered more, and cause blurring and noise problems in conventional x-ray CAT devices. Using conventional x-ray sources, it is difficult to hold a constant high voltage for pulsed operation, leading to a mixture of high energy x-rays with low energy x-rays that cause scattering-related noise problems. The use of source and detector aperture collimated x-ray beams reduces this problem significantly. The use of vanes can further improve performance, as more fully described in our co-pending application U.S. patent application Ser. No. 10/933,036.

However, by using a detector aperture to define a narrow beam, such scattered x-rays do not pass through the detector aperture, reducing noise and increasing resolution. A narrow beam, which in this example is a beam having a diameter of less than 5 mm, such as between approximately 1 mm and approximately 1.5 mm, also allows use of a high photon flux with detectors capable of handling a high photon flux while concurrently performing emission imaging with detectors having a relatively low count rate capability. The detector aperture may be approximately the same dimension as the source aperture, within the plane of an image slice (such as using similar slot widths), so as to collimate the transmitted beam and avoid any substantial beam divergence through the field of view.

Further, a pulsed x-ray source can be used in an improved x-ray CAT scanner. Using source and detector aperture collimation to provide a narrow beam, for example between 1 and 1.5 mm, and coordinated motion of the apertures to track the collimated beam as it is scanned through the field of view, problems of low energy x-ray scattering are reduced, and radiation exposure of the subject is also reduced. The imaging time may be longer than conventional apparatus, but the cost of such an instrument can be a small fraction of conventional apparatus.

Apparatus according to the present invention, in particular x-ray transmission imaging apparatus, may be used with existing SPECT detectors, such as those described in my co-pending and issued patent applications, for example U.S. patent application Ser. No. 10/933,036 "Single Photon Emission Computed Tomography System" to Juni. The x-ray sources, source apertures, and detectors (or associated detector apertures) can be arranged in an arcuate arrangement, which can be combined with existing SPECT systems, for example as described in U.S. patent application Ser. No. 10/933,036. As used herein, the term arcuate is used broadly to include circular arc segments, complete circular arrangements, ovoids, other curved segments, and other geometric forms approximating a curved segment. Apparatus according to the present invention, in particular x-ray transmission imaging apparatus, may also be used with more conventional existing SPECT detectors, including those with generally flat detector surfaces.

Even though examples show curved arrangement of detectors and source apertures, there is nothing about this design that mandates the detectors be curved. The same principle can be used with flat detectors. In such examples, the x-ray sources are arranged in a flat line and the source apertures are on a flat sheet.

The prior art on x-ray CAT scanning generally emphasizes the value of completing the scan as quickly as possible. Hence, there is no motivation to use a pulsed x-ray source, particularly with a low duty cycle, as this slows the completion of the scan. However, as discussed elsewhere in more detail, the combination of a pulsed x-ray CAT scan and emission image gives valuable and improved data with a possibly insignificant time penalty relative to the time needed to collect the emission image. Hence, an improved method of collecting emission and radiation transmission data from a subject comprises providing a pulsed radiation source, collecting radiation transmission data when the source is on, and collecting emission data when the source is off.

An apparatus, according to an embodiment of the present invention, for imaging a subject within a field of view comprises a radiation source positioned adjacent to the field of view, and a source mask located between the radiation source and the field of view, having at least one source aperture defined therethrough through which radiation from the radiation source passes. An emission detector adjacent to the field of view detects emission from the subject that is incident on the emission detector, and a radiation detector is located so as to detect radiation that has passed through the field of view. A radiation attenuation image can be formed from the radiation detector signal, and an emission image can be concurrently formed from the emission detector signal. The radiation detector and emission detector may both be provided by a single detector assembly, for example a detector assembly that provides a time-indexed signal that corresponds to emission when the radiation source is turned off, and to radiation attenuation when the radiation source is turned on. The radiation source may be pulsed. In other examples, the radiation detector is situated so as to receive the radiation beam after it has passed through the field of view, and an emission detector is located so as to receive emission from the subject. The radiation is shielded from the emission detector by a radiation shield and/or the radiation detector, the shielding moving as the radiation path direction is swept through the field of view. The shielding may block a proportion of the emission from the emission detector, which effect may be neglected or compensated for if desired. The radiation attenuation image can be used to correct for attenuation effects in the emission image, if desired.

In embodiments of the present invention, the radiation source is an x-ray source, the radiation being x-rays which are transmitted through the body. The emissions comprise gamma emissions, for example emitted by radio-labeled materials within the subject. A detector assembly may comprise an x-ray transmission detector and a gamma emission detector. In other configurations, the emission detector is a gamma detector for gamma radiation, and the x-ray transmission detector is located between the gamma detector and the field of view, positioned to receive the x-rays from an x-ray source passing through the source aperture. An x-ray shield is positioned so as to substantially or completely block the x-rays from striking the emission detector, while allowing emission from the field of view to reach the emission detector. Hence, concurrent emission and x-ray attenuation (transmission) images can be provided by a single apparatus. The x-ray attenuation data may be used to increase the accuracy of the gamma emission images by allowing compensation for attenuation variability within the subject.

In embodiments of the present invention, the emission detector is a gamma detector, the emission being gamma radiation, and the apparatus allows both x-ray and gamma information to be determined for the subject. Embodiments of the present invention allow concurrent gamma and x-ray imaging, where the x-ray imaging time and gamma imaging time are similar and substantially overlap.

An actuator can be used to move the source mask relative to the x-ray source, to change the path direction of x-rays through the field of view, with the x-ray detector moving in response to the change in path direction so that the x-ray detector continues to receive the x-rays. The detector shield may also move to block the emission detector from x-rays. The x-ray detector can be mounted on the x-ray shield, the combined assembly being moved by the same or a different actuator as the source mask.

A first signal from the emission detector can be used to provide an emission image (such as a gamma image) of the subject, while a second signal from the x-ray detector can be used to provide an x-ray transmission image, such as an x-ray attenuation image obtained concurrently with the emission image. Concurrent medical imaging of a living subject allows the x-ray and emission images to be readily interpreted together, allowing more accurate diagnosis of a subject condition. The images may be superimposed or presented side by side to a practitioner. Further, the x-ray attenuation image can be used to improve the accuracy of a gamma image, by compensating for density variations and variable attenuation of the gamma signal.

The x-ray shield may be configured in various ways. The x-ray detector, including the housing thereof, may provide the x-ray shield. The x-ray detector may be mounted on a metal or similar plate. The x-ray shield may only block a small portion of the field of view from the emission detector, and the x-ray path and x-ray shield sweep across the front (emission receiving surface) of the emission detector. Alternatively, the x-ray shield may includes a plurality of shield apertures therethrough, the shield apertures being positioned so as to allow emission from the field of view to reach the emission detector while preventing x-rays from reaching the emission detector.

The x-ray source is pulsed between an on state and an off state, so as to provide x-ray pulses having a pulse duration, the pulses separated by a pulse interval during which the x-ray source is in the off state. The pulse duration can be between approximately 0.01 milliseconds and approximately 200 milliseconds, for example between approximately 0.5-20 milliseconds. The duty cycle (on time/off time) can be small, for example less than 0.01. For example, the x-ray source(s) can be turned on for 1 millisecond every second, giving a duty cycle of 0.001.

Gamma imaging is typically a low photon flux method compared with x-ray imaging, so that a pulsed x-ray source allows an x-ray image to be collected over an x-ray imaging time that is concurrent with the gamma imaging time. The x-ray imaging time is considered as the time over which the x-ray image is formed, from the start of the imaging to the end of the imaging process. The lower the duty cycle, the longer the x-ray imaging time becomes, for the same total number of x-ray photons used to form the x-ray image. To further reduce x-ray induced noise (scattered x-rays that would interfere with the emission image) during collection of the emission image, the emission image may be collected using signals only collected during the pulse-off interval. The time periods for emission imaging and transmission imaging may then be effectively be interleaved, with an imaging duty cycle (transmission imaging time/emission imaging time) tracking the duty cycle of the x-ray source. Alternatively, if the emission detector is substantially shielded from the x-rays, emission imaging may be continuous, with transmission imaging only when the source is on.

For example, a scintillation gamma detector may operate with a flux of 100,000 photons/second, whereas x-ray detection may operate with a flux of millions of photons per second. By collimating the x-ray beam with source and detector apertures so that the x-ray beam does not strike the gamma detector, simultaneous x-ray and gamma imaging may be performed. For example, an x-ray pulse of millisecond scale pulse length may be provided for each angular projection needed, with a new angular projection obtained approximately each second. The x-ray image is built up using millisecond data accumulations distributed over the longer time needed to form an emission image. Electronic circuitry for generating images from detector signals is well known in the imaging art and will not be described further.

In other embodiments, one or more x-ray sources may be used, and the source mask may include a plurality of source apertures providing x-rays having a plurality of path directions through the field of view. Moving the source mask relative to the x-ray source modifies the plurality of path directions through the field of view. A plurality of x-ray detectors can be positioned to detect x-rays along all or some of the plurality of path directions.

A further exemplary apparatus for characterizing a subject located within a field of view comprises an x-ray source, a source mask located between the x-ray source and the field of view, having a source aperture therethrough, so that x-rays passing through the source aperture enter the field of view, and a detector located adjacent the field of view, and a detector shield located between the field of view and the detector. The detector shield has one or more a detector apertures therethrough, so that x-rays striking the detector have a path direction through the field of view defined by the source aperture and the detector aperture. The detector is preferably positioned to receive x-rays passing through the source aperture and through the detector aperture. An actuator moves the source mask relative to the x-ray source, so as to modify the path direction of x-rays through the field of view.

The apparatus may further comprise a plurality of x-ray sources, and a plurality of source apertures within the source mask, so that the actuator moves the source mask relative to the x-ray sources, so as to modify a plurality of path directions through the field of view. The plurality of x-ray sources can be arranged substantially in a first arc, with the plurality of source apertures are arranged substantially in a second arc, the second arc being inside and concentric with the first arc. The detector shield may further have a plurality of detector apertures therethrough. The detector can part of an arcuate and/or circular detector assembly, which may comprise a plurality of detectors arranged around a third arc, and positioned so as to receive x-rays that have passed through the field of view, or may comprise one or more detectors having a arcuate form. The x-ray source can be pulsed between an on state and an off state, so as to provide x-ray pulses having a pulse duration, the pulses separated by a pulse interval during which the x-ray source is in the off state. The detector assembly may be sensitive to both x-rays and gamma photons, for example being used to form an x-ray image when the x-ray source is on, and a gamma image when the x-ray source is off, so as to provide simultaneously generated x-ray and gamma images of the field of view.

An apparatus for providing a gamma emission image and an x-ray transmission image of a field of view comprises an x-ray source, pulsed between an on state and an off state, so as to provide x-ray pulses having a pulse duration, the pulses separated by a pulse interval during which the x-ray source is in the off state; an emission detector, providing an emission detector signal in response to gamma photons incident on the emission detector, and an x-ray detector, providing an x-ray detector signal in response to transmitted x-rays incident on the x-ray detector. Electronic circuitry is operable to form an x-ray transmission image of the field of view from the x-ray detector signal, and to form a gamma emission image of the field of view from the emission detector signal. The images may be formed concurrently, over similar x-ray and gamma imaging times.

DETAILED DESCRIPTION OF THE INVENTION

Embodiments of the present invention provide an improved imaging of a subject. Imaging may be carried out using two electromagnetic wavelength regions, such as x-ray imaging and gamma imaging (such as SPECT). X-ray attenuation measurements can be used to provide an improved SPECT image, by allowing correction for attenuation variability of the gamma photons in a subject. The attenuation coefficient may be assumed to be the same for gamma photons or x-ray photons, or a model of the subject used to convert between attenuation coefficients so as to make an attenuation correction.

In representative embodiments of the present invention, attenuation measurements are carried out by determining attenuation of a radiation beam through the subject. A radiation source is located adjacent a field of view, and radiation from the radiation source is detected after being transmitted through the field of view. By varying the path direction of the radiation through the field of view, a radiation transmission (attenuation) image of a subject in the field of view can be obtained. Concurrently, the field of view can be imaged using emission (which may be the same or a different type from the radiation provided from the radiation source) from the subject in the field of view. In examples of the present invention, the transmitted radiation may be x-rays, and the emissions may be gamma emissions. However, in other examples, the emissions imaged may be fluorescence, thermal emission, other IR emission, visible, or other emission by which the subject may be imaged. The radiation used to determine radiation attenuation of the subject can be x-rays, or other radiation such as any wavelength of laser radiation, IR, visible, UV, THz, microwave, or nuclear radiation. The radiation attenuation measurements may then be used to correct the emission imaging, by compensating in variations of emission attenuation over the subject or any surrounding material for which measurements are made. Alternatively, the radiation attenuation and emission images may be determined separately, without correction of the emission image, for improved analysis of the subject.

Figure 1:
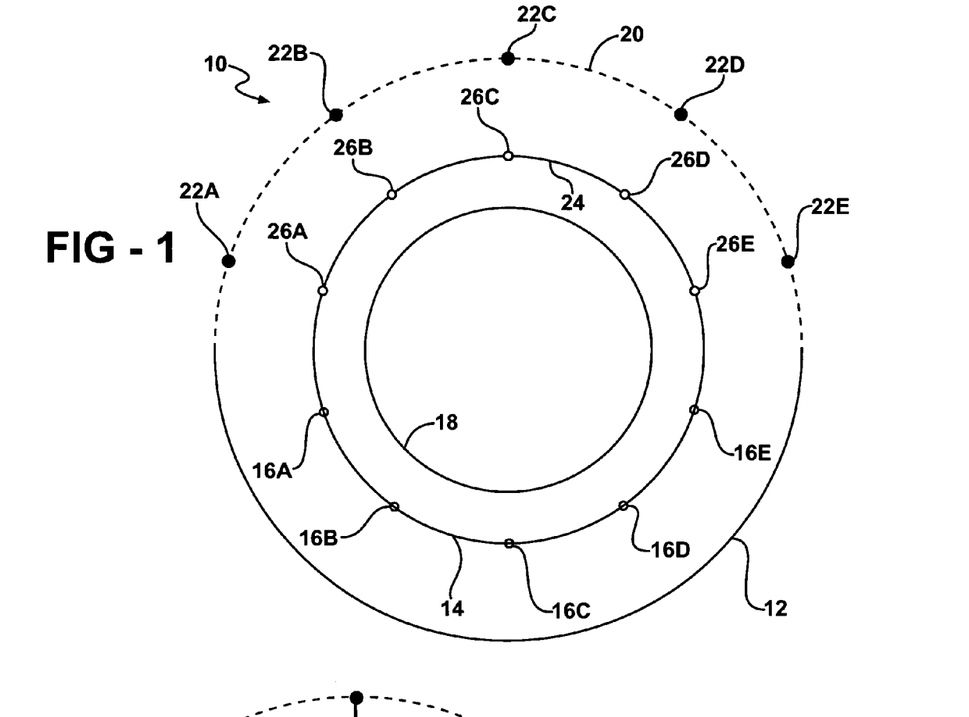
FIG. 1 is a schematic of an apparatus having a plurality of x-ray sources arranged in an arc.

FIG. 1 schematically illustrates an apparatus 10 configured to also provide x-ray attenuation data concurrently with SPECT imaging. The apparatus may be a modified version of a SPECT apparatus as described in our co-pending applications.

The apparatus includes an arcuate detector assembly 12, which may be a plurality of detectors arranged along an arc or one or more arcuate detectors. The apparatus also includes an arcuate detector shield 14 having detector apertures therethrough, the detector apertures shown as small circles 16A-16E and configured as a detector aperture arc.

The lower half of the apparatus 10 in FIG. 1, including detector assembly 12 and detector shield 14, may correspond to an embodiment of a SPECT apparatus. FIG. 1 is schematic in nature and not necessarily to scale. A portion of the SPECT apparatus may be constructed according to any of the examples discussed in U.S. Prov. App. 60/607,319 and U.S. patent application Ser. No. 10/933,036.

The field of view, in which a subject is positioned, is shown at 18. The schematic view of FIG. 1 may be considered, for descriptive convenience, to be a top view with the detector apertures 16A-16E being generally vertical slots in the detector shield 14. While not illustrated, the apparatus 10 also preferably includes "horizontal" collimation vanes between the field of view and the detector assembly 12. These are typically located between the detector shield 14 and the detector assembly 12. Collimation vanes are described, for example, in U.S. patent application Ser. No. 10/933,036. The detector shield 14 and/or the detector assembly 12 may rotate relative to each other and/or relative to the field of view 18, so as to sweep the detected x-ray paths (equivalent to the lines of response of the detector assembly) across the field of view 18.

The apparatus 10 further includes an x-ray source arc 20 with a plurality of x-ray sources 22A-22E arranged along the arc. It also includes a source mask arc 24 having a plurality of source apertures 26A-26E provided through the source mask 24. The source apertures are schematically represented by circles, and may be slots or other apertures through which x-rays pass through into the field of view 18.

While the source mask 20 is shown as generally continuous with the detector assembly 12, and the source mask 24 is shown continuous with the detector shield 14, they are preferably all individual components, and may overlap to some extent. For patient access purposes, the various components of the apparatus may nest or retract so as to provide an access opening to the field of view 18. Alternatively, in some embodiments, the detector assembly 12 and x-ray source arc 20 may be interconnected and/or the detector shield 14 and source mask 24 may be interconnected.

Again, while not illustrated, horizontal collimating vanes can be provided between the field of view 18 and the x-ray sources 22A-22E. The horizontal vanes collimate the x-ray sources into planes, parallel to the plane of the illustration, while the source apertures limit the x-ray paths through the field of view to narrow beams of x-rays which may also be termed source lines. The x-ray mask arc 24 blocks x-rays from the x-ray sources that not aligned with the source apertures.

By rotating the x-ray sources and/or the source apertures relative to each other and/or relative to the field of view, the path directions of for x-rays from the x-ray sources may be swept across the field of view.

According to a further aspect of the present invention, the movement of the arcs 12, 14, 20 and 24 can be coordinated such that the narrow x-ray beams extend through the source apertures and into one of the detector apertures, so as to be received by the detector assembly 12. This use of narrow x-ray beams provides several benefits. First, it limits the x-ray exposure of the patient. Secondly, by collimating the x-rays both at the source and at the receiving end, scattering of the x-rays in the patient has significantly less effect on the attenuation data collected during this process.

The figure shows five x-ray sources, five source apertures, and five detector apertures. The numbers of each may be varied. For example, a single x-ray source may be used with a plurality of source apertures. The number of source apertures need not match the number of detector apertures.

Figure 2:
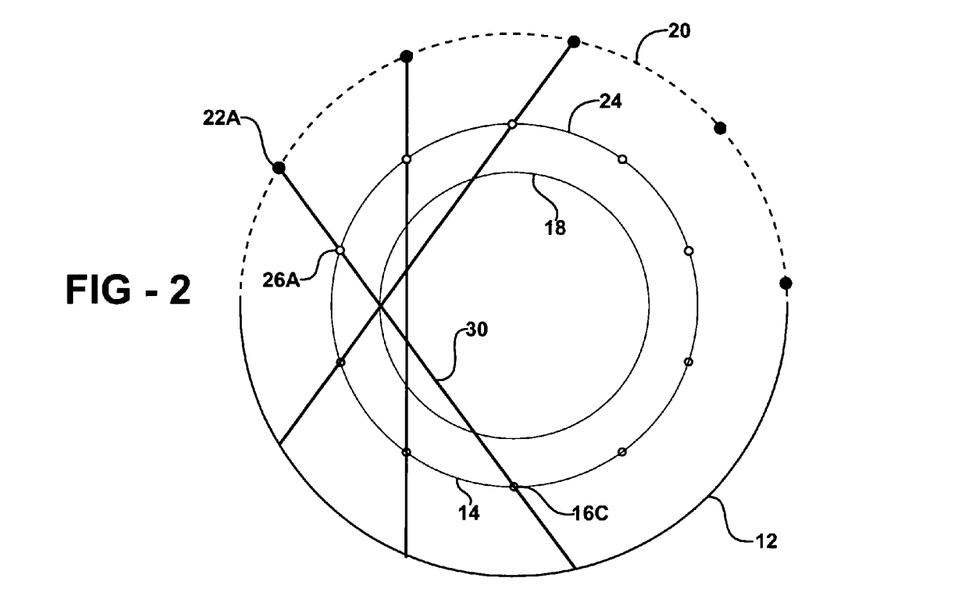
FIG. 2 illustrates path directions of x-rays through the field of view of the apparatus shown in FIG. 1.

FIG. 2 shows three x-ray sources emitting narrow x-ray beams through corresponding source apertures, such that the beams are aligned with corresponding detector apertures so as to strike the detector assembly 12. Only three x-ray sources are shown for illustrative clarity. As a representative example, x-ray source 22A emits x-rays passing along path direction 30 through source aperture 26A and detector aperture 16C to detector assembly 12. In practice, each of the x-ray sources 22 may emit x-rays in a plurality of directions, with the horizontal collimators collimating the x-rays to a plane, and the detector apertures further collimating them to a narrow beam. However, the narrow beams resulting from the collimation are illustrated for ease. As will be clear to those of skill in the art, the x-rays from one source may pass through more than one source aperture so as to create more than one path direction through the field of view. Changes in relative positions of x-ray source, source apertures, and detector apertures, for example through relative rotation (or angular scans) thereof, can be used to collect data for reconstruction of an x-ray attenuation image.

Three-dimensional images can be formed using detector assemblies extending normal to the plane of the illustration. Apertures may be slots normal to the plane of the illustration, or curved slots as described in our co-pending U.S. patent application Ser. No. 10/933,036. The number of x-ray sources in this example is shown as five. In other examples, a single source may be used, and scanned over a larger range, or any plurality of x-ray sources used.

FIGS. 3-6 illustrate the beams being swept across the field of view 18 in various positions. In one preferred embodiment, the various arcs move at different speeds so as to index the x-ray beams such that they each encounter one of the detector apertures. In one example, the x-ray sources, arranged in a source arc, move together at a relatively high speed, while the x-ray mask arc and corresponding source apertures move at a medium speed, and the detector apertures move at a slower speed. This allows every projection angle to be obtained for a complete reconstruction of an x-ray image. The rates of rotation can be selected so that the x-ray sources, source apertures, and detector apertures are lined up throughout the scan, increasing efficiency. No x-ray source needs to be turned off because a transmitted beam is not in register with an x-ray detector. Other combinations will be clear to those of skill in the art.

Figure 3:
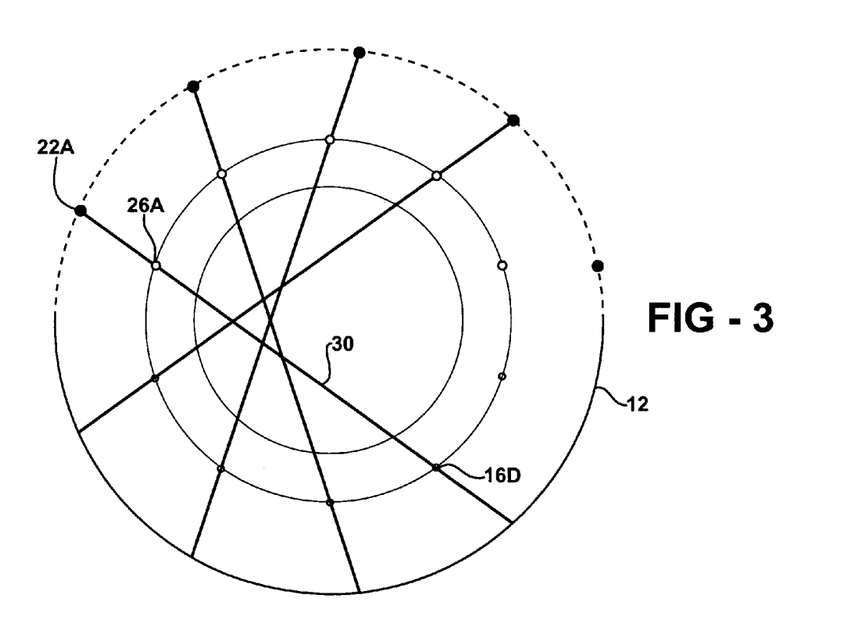
FIGS. 3-6 show changing path directions as the relative positions of x-ray sources and source apertures are changed.
Figure 4:
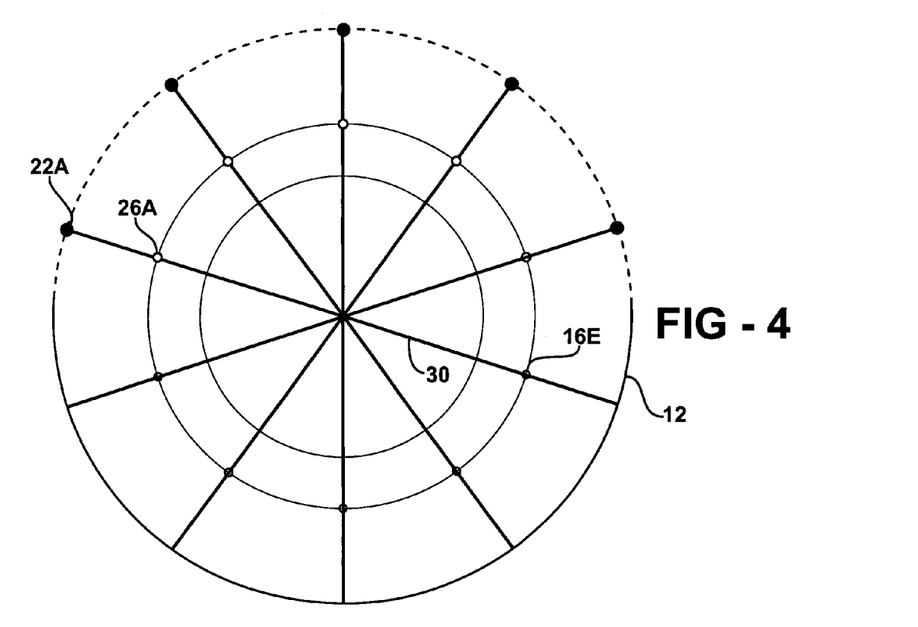
Figure 5:
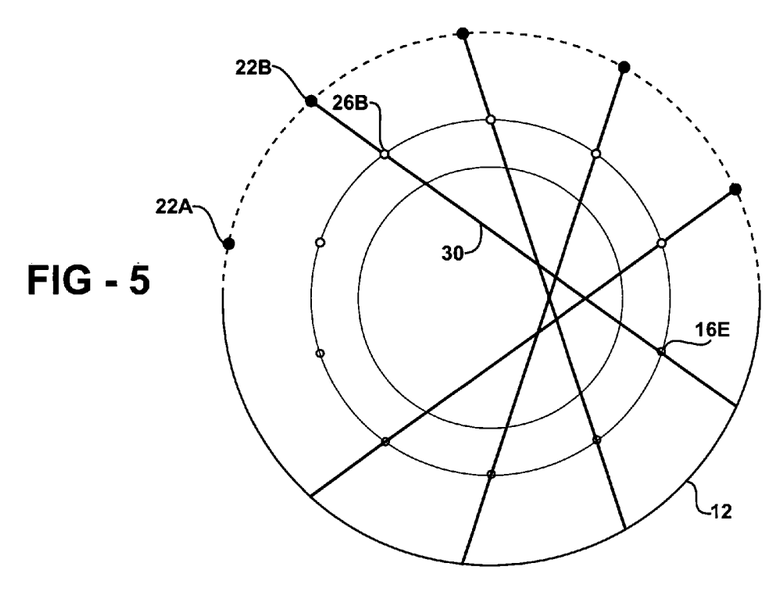
Figure 6:
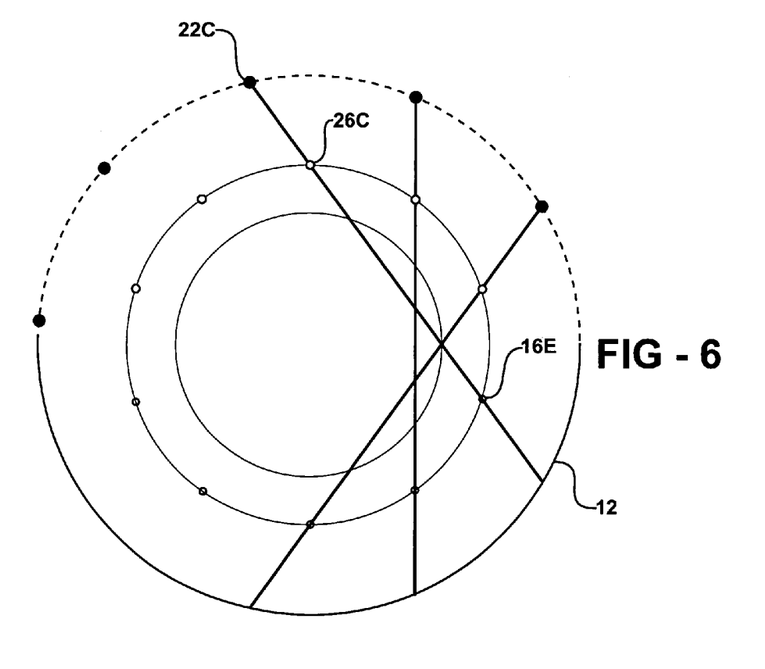

FIG. 3 shows x-rays from x-ray source 22A passing through source aperture 26A and detector aperture 16D to detector assembly 12. FIG. 4 shows x-rays from x-ray source 22A passing through source aperture 26A and detector aperture 16E to the detector assembly. In FIG. 5, no x-rays from x-ray source 22A reach the detector assembly. X-rays from source 22B pass through source aperture 26B and detector aperture 16E to detector assembly 12. In FIG. 6, x-rays from source 22C pass through source aperture 26C and detector aperture 16E to detector assembly 12. The path direction discussed for each figure is labeled 30 in each figure, and this path direction changes with changes in the relative configuration of the sources, source apertures, and detector apertures.

The x-ray attenuation measurements of an embodiment of the present invention can be made using a variety of approaches. In one approach, an approach similar to a CAT scan approach can be used, wherein the x-ray sources are all turned on continuously and the various arcs are rotated such that all combinations of angles of the patient are passed through by x-ray beams so that a full set of attenuation data is obtained. Then, the x-ray sources may be turned off, and the detectors in the detector assembly 12 are used to obtain a SPECT image. In this approach, the detector assembly 12 is used to detect both transmitted x-rays and gamma emissions from the field of view. The x-ray sources typically provide a much higher level of x-rays than the level of gamma emissions from the patient, and therefore substantially all of the counts detected by the detectors in the arc 12 may be assumed to be x-ray counts, while the x-ray sources are turned on. Hence, a detector signal from the detector assembly 12 may be assumed to be due to gamma emissions when the x-ray sources are turned off, and from x-rays when the x-ray sources are turned on. Corrections to the x-ray data due to a baseline gamma emission may be carried out, as will be clear to those skilled in the arts.

Alternatively, since x-rays and gamma emissions may have different photon energies, the detector signals provided by the detector assembly may contain information about x-ray and gamma signals simultaneously. Gamma and x-ray information may both be extracted from signals from a detector assembly, for example from using pulse strength analysis, pulse shape discrimination, or other method, for example using a layered detector having more than one detector material (such as a plurality of scintillator materials) allowing for energy discrimination between detected photons.

The x-ray sources may be pulsed, such that they turn on for a very short period, such as 0.5-20 milliseconds, for example 1 millisecond, at a relatively high level, intermittently during a SPECT scan. The short "on" period may be longer or shorter, such as in the range of 0.01 to 200 milliseconds. Preferably, the x-ray source is turned off for an "off" period between the "on" periods. The "off" periods are preferably substantially longer than the "on" periods. When the x-ray sources are turned on, substantially all "counts" detected by the detector assembly 12 may be assumed to be x-ray counts. The x-rays may be on for a very small fraction of the total imaging time, spread out over the entire imaging, such that they provide a time-averaged attenuation image without either substantially lengthening the overall imaging time or reducing the SPECT imaging accuracy. The pulsing of the x-ray sources at high energy and short duration (short duty cycle) also provides the benefit that an x-ray source with a lower rating may be used and/or the x-ray source will last longer.

Figure 7:
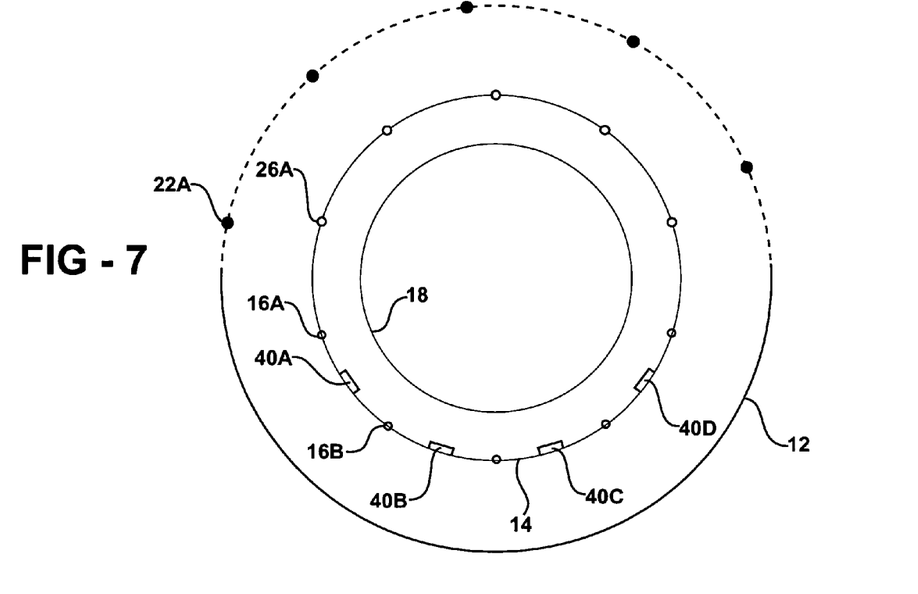
FIG. 7 shows an apparatus having a detector assembly and further having x-ray detectors in front of the detector assembly.

FIG. 7 shows an alternative embodiment of the present invention. In this embodiment, x-ray sensors 40A-40D are provided on the inside of the detector shield 14 between the detector apertures. For example, x-ray detector 40A is located between detector apertures 16A and 16B. In this embodiment, the x-ray beams from the x-ray sources are indexed so as to strike the x-ray detectors 40A-4D, and not to pass through the detector apertures to the detector assembly 12. The detector assembly is used to detect gamma photons emitted from the subject.

In other embodiments, horizontal collimators are provided between the x-ray detectors and the field of view. For example, as discussed with respect to various embodiments described in U.S. patent application Ser. No. 10/933,036, the detector shield, referred to as an aperture arc therein, may be positioned further from the field of view with collimation vanes between the aperture arc and the field of view instead of, or in addition to, collimating vanes between the aperture arc and the detector assembly.

In the apparatus of FIG. 7, the x-rays may be transmitted at the same time that SPECT imaging is conducted, since different sensing systems are used. The detector assembly 12 is used to detect gamma emissions, and is shielded from x-rays by the detector shield 14. The detector apertures may be enlarged, for example to occupy a majority of the angular range between the x-ray detectors, so as to pass more gamma emissions to the detector assembly.

As a further alternative, the x-ray sensors may be arranged differently, or may cover a larger portion of the aperture arc, such that x-rays at more angles may be detected at the same time.

Figure 8:
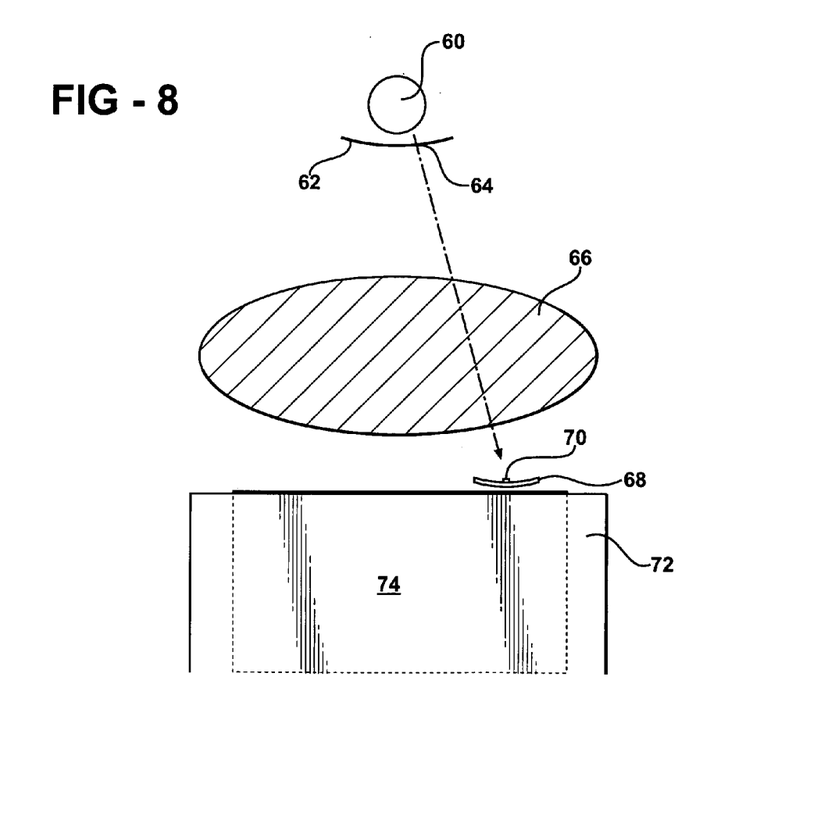
FIG. 8 shows an apparatus having a scanning x-ray beam and a shield to prevent the x-ray beam from falling on a detector.

FIG. 8 shows an apparatus comprising an x-ray source 60, providing an x-ray beam which passes through a source aperture 64 (a slot) in source mask 62, passing through subject 66 (which may be a patient such as a human or pet, for example a dog, cat, or other mammal, or organ or other part thereof, or inanimate object such as a package, suitcase, food product, and the like), and incident on an x-ray detector assembly. The x-ray detector assembly comprises an x-ray detector 70 (such as a semiconductor detector) and detector shield 68 (for example, a lead shield). The source mask 62 acts as a collimator or focusing device by allowing x-rays to pass through the source aperture 64. As known to those of skill in the art, the shield 62 is preferably positioned far enough from the x-ray source 60 to achieve desired collimation or focusing of the x-rays. This distance may be greater than the distance shown in FIG. 8, which need not be to scale.

Moving the source mask rather than the source is advantageous, since the source mask is more easily moved. The gamma camera 72, including gamma detector 74, is shielded from the x-ray beam by the detector shield 68 as the x-ray beam performs an angular scan of the subject. The x-ray beam is prevented from passing through apertures in the gamma camera to the gamma detector material.

In an example apparatus, the x-ray detector 70 is a type that is not saturated (or paralyzed) by direct incidence of the x-ray beam. Example x-ray detector materials include CZT (cadmium zinc telluride), zinc telluride, other chalcogenides, other semiconductors, or other high speed x-ray detector material. The x-ray detector may alternatively consist of a gas-type proportional detector device. The x-ray beam can be pulsed, and the pulse frequency may be inversely correlated with the recovery time of the x-ray detector material. Other approaches which may be used in x-ray detectors include microcalorimeters (including single photon calorimeters, which generally require cooling), microchannel plate devices, proportional counters, semiconductor detectors (including CMOS), scintillators, and phosphors.

The configuration of FIG. 8 allows the pulse frequency of the x-ray beam to be independent of the recovery time of the gamma detector to direct exposure to the x-ray beam, a situation that is prevented by this configuration. Hence, slow gamma detector materials (relative to the x-ray detector material) can be used with a rapidly pulsed x-ray beam. The shielding of the gamma detector allows a gamma detector material to be used that would be otherwise be saturated by direct incidence of the x-ray beam. For example, sodium iodide, cesium iodide, bismuth germanate or other scintillation material such as a plastic scintillator can be used as the gamma detector material. The configuration of FIG. 7 also allows the use of high power and rapidly pulsed x-ray sources, without saturation of the material used to sense the SPECT information, since the x-rays do not impinge on the material used to sense the SPECT information. Instead, the x-rays preferably impinge on receivers 40 between the slots 16. Alternatively, when a gamma detector comprising non-paralyzing material is used to obtain SPECT information, x-ray shielding may not be required.

The gamma detector 74 does not receive the x-ray beam directly, due to the collimation of the x-ray beam by slot 64, and the shielding of shield 68. Additional collimation, for example using other slots, slot arrays, apertures, metal capillaries, shielding plates, directional x-ray sources, and the like, can be provided. The x-ray detector assembly may further comprise one or more x-ray collimators in front of the x-ray detector 70.

Additional shielding of the gamma camera can also be provided, if desired, for example to reduce incidence of stray scattered x-rays on the gamma detector.

Figure 9A:
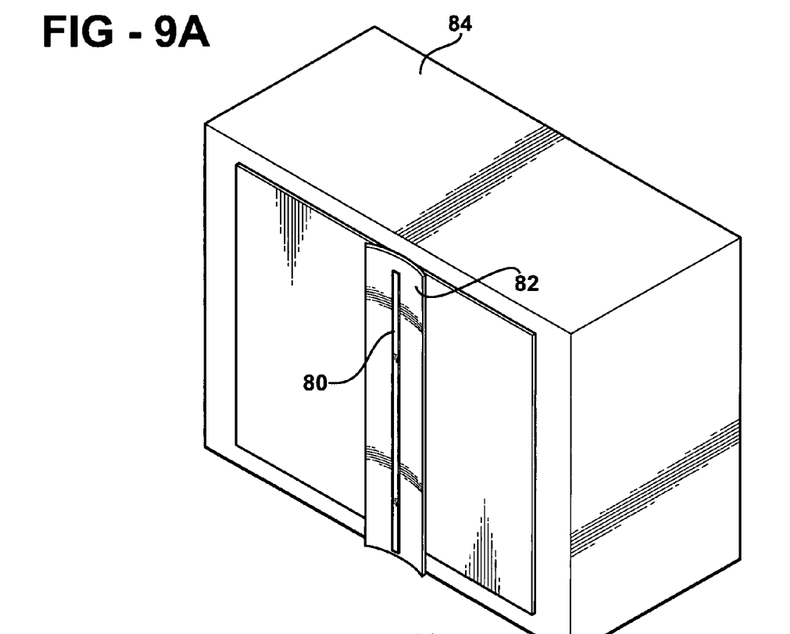
FIGS. 9A and 9B shows an x-ray shield and x-ray detector mounted thereon moving across the detection face of a detector.
Figure 9B:
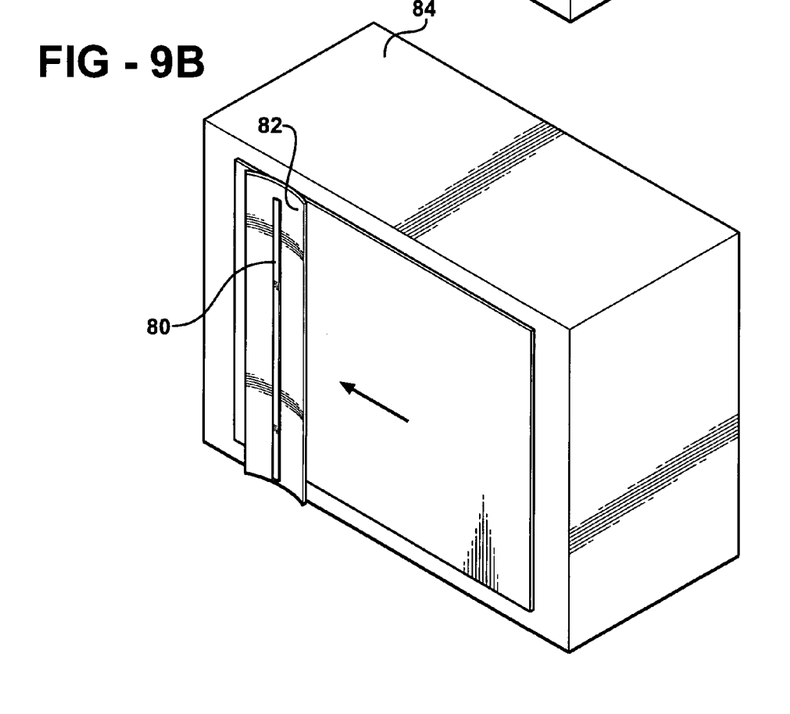

FIG. 9A shows a view of an x-ray detector assembly (comprising detector shield 82 and x-ray detector 80) in front of an emission detector 84. In this example, the emission detector is a gamma camera. FIG. 9B shows the detector shield 82 and x-ray detector 80 moved to one side of the gamma camera 84, corresponding to an angular sweep of the x-ray beam across a field of view, relative FIG. 9A.

In this example, the x-ray beam sweeps through a scan angle. In this example, the x-ray detector may comprise a material that is responsive to a high photon flux, such as a strip of semiconductor material, having a vertical orientation as shown by the figure. The x-ray detector assembly scans with an angular motion correlated with the angular scan of the x-ray beam, so that the x-ray beam remains incident on the x-ray detector during the angular scan (at least for angles of interest, or for angles where the x-ray beam would otherwise fall on the gamma camera). The detector shield may be a lead shield, or comprise another x-ray absorbing material.

As the x-ray detector assembly passes in front of apertures of the gamma camera, the aperture will be momentarily blocked off (for example, for 2-3 seconds). However, this does not significantly impair the operation of the gamma camera, and signals from the gamma camera can be numerically corrected for the temporary blocking of apertures therein. The apparatus can be configured such that most of the photons from the field of view reach the gamma camera, and are not blocked by the detector shield.

The gamma camera, an example of an emission detector, detects gamma emission and provides some spatial distribution information for the detected gamma photons. A gamma camera may comprise a scintillation crystal, for example thallium-doped sodium iodide or cesium iodide, an array of detector collimators between the scintillation crystal and the field of view, and an array of photomultiplier tubes to detect scintillation photons created by gamma radiation in the scintillation crystal. The scintillation photons may be visible, and may be detected by any optical detector, including photodiodes and other photon-responsive semiconductor devices. The gamma camera provides detector signals correlated with the spatial distribution of detected scintillation photons, and these detector signals may be used to form a two-dimensional or three-dimensional image. Electronic circuitry can then be used to obtain a gamma image of the subject from the detector signals, using methods known in the art. Embodiments of the present invention may be used for two and three-dimensional gamma and/or x-ray imaging of a subject.

A detector assembly may comprise one or more two-dimensional detector arrays. The detector arrays may comprise emission detectors, selected according to the wavelength of detected radiation. For gamma emission detectors, solid state detectors comprising CZT (cadmium zinc telluride), or cadmium telluride, or other chalcogenides may be used. Detectors may also comprise scintillation materials such as sodium iodide or cesium iodide, with associated scintillation emission detectors such as photomultiplier tubes or other photo-detectors such as photodiodes. A detector assembly may comprise a plurality of pieces of scintillation material assembled side-by-side, or a single large curved crystal of scintillation material. Scintillation detectors may also comprise position sensitive scintillation emission detectors, and/or optical fiber arrays to guide scintillation photons to appropriate detectors.

Hence, an improved combined CAT and SPECT device comprises an x-ray source providing an x-ray beam, a mechanism to provide an angular scan of the x-ray beam through the subject, a gamma camera, and an x-ray detector assembly having an angular motion correlated with the angular scan of the x-ray beam, the x-ray detector comprising a high-speed x-ray detector and an x-ray shield preventing direct incidence of the x-ray beam on the gamma camera. In other examples, the gamma camera may be omitted, and/or other detector system used, for example a PET imager, thermal imager, video or other imaging system.

Preferably, the present approaches may also be used to provide combination CT and PET apparatus. In either combination, the CT/x-ray portion allows attenuation correction and also allows localization of body structures in the area of interest. For example, if a SPECT scan locates an area of concern, it is beneficial to have a CT scan of the same area to locate the relative positions of body organs and bone structure. The present invention offers this capability. As a further alternative, any of the designs presented herein may be used as a CT/x-ray apparatus without the SPECT or PET aspects. Either the designs may be used in a CT/x-ray mode, without operating the SPECT or PET portions, or a device may be provided with only the CT/x-ray capabilities. That is, the designs presented herein provide a novel and highly useful CT apparatus, independent of the other aspects discussed herein.

The mechanism to provide an angular scan of the x-ray beam may comprise a rotating structure including an aperture, aperture array, x-ray reflector, directional x-ray source, or other structure.

In other examples, two or more x-ray beams may be scanned through the subject, with associated x-ray detector assemblies preventing direct incidence on the gamma camera.

In other examples, the x-ray beam may be a pencil-like beam, with appropriate collimation, for example by rounded apertures, and may be scanned through one or more planes, such as two orthogonal planes. In a further example, the x-ray source may move linearly side to side (with respect to FIG. 8), and may move with the receiver or counter thereto. As one example, the source may move to multiple positions with the receiver scanning for each position. As yet a further alternative, the receiver or receivers may be stationary with the source moving, though the illustrated embodiment is currently preferred.

In an example application, the subject being imaged may be an organ of a patient, such as the heart. As described for example in U.S. patent application Ser. No. 10/933,036, the patient is injected with a radioactive substance, which is taken up by heart muscle as it uses oxygen. Gamma emission then originates from this heart tissue and may be detected by gamma detectors. The detected gamma emissions are then used to reconstruct an image of the heart muscle. However, the patient's heart is surrounded by various types of tissue of various densities. This surrounding tissue absorbs or otherwise attenuates the radioactive emissions in a non-uniform manner, complicating the accurate reconstruction of an image. This is serious problem in medical imaging. However, apparatus according to embodiments of the present invention allow concurrent x-ray attenuation and gamma imaging of a patient to be carried out, allowing the gamma image to be corrected for variations of density in surrounding material, such as tissue.

Apparatus according to embodiments of the present invention allow x-ray images, such as x-ray attenuation images, to be obtained concurrently with gamma imaging. Pulsing of the x-ray source allow the x-ray image to be obtained over a time-scale similar for that needed to obtain a gamma image.

In other examples, x-ray images can be combined with dynamic SPECT imaging, for example to provided x-ray and gamma image data derived movies of organ function over a common time-scale.

In other examples, gated SPECT imaging can be combined with pulsed x-ray image data to obtain concurrent images of the same stage of a repetitive process, for example a particular stage of a heart beat. The x-ray source may have a long off period at times not of interest.

Examples discussed above show a combination of x-ray detectors, for example for CT imaging or other scan, and gamma cameras, for example for SPECT medical imaging. However, examples of the present invention also include stand-alone CT scanners. The SPECT imaging, or other gamma imaging function, of any apparatus disclosed herein is optional. Applications include imaging of the heart, brain, kidney, or other bodily organ or function thereof.

Other examples of the present invention may be used with different types of radiation. For example, laser attenuation measurements can be made by scanning laser radiation through a subject, with a laser radiation detector and optional associated radiation shield moving with the laser beam. An emission detector, or other detector, may concurrently be used to obtain image data using radiation emitted from the subject, for example thermal radiation, laser-induced fluorescence, IR, microwave, terahertz (THz), or other radiation. Apparatus according to the present invention allows laser attenuation and radiation imaging to be performed concurrently. In other examples of the present invention, x-ray imaging may be combined with PET (positron emission tomography) imaging.

Further Details of Medical Imaging

Further aspects of medical imaging devices, which may be used in embodiments of the present invention, are described in my co-pending patent applications, including U.S. patent application Ser. Nos. 10/933,036 and 10/872,253 (both entitled "Single photon emission computed tomography system"); U.S. Ser. No. 10/993,012 ("Edge effects treatment for crystals"); U.S. Ser. No. 10/358,961; and U.S. Pat. Nos. 6,525,321 and 6,525,320 (both entitled "Single photon emission computed tomography system"), the contents of all of which are incorporated herein by reference in their entirety.

The field of view may be configured to contain the torso of a human patient, so as to perform cardiac imaging. The torso may be horizontal or vertical for imaging. In one embodiment, the detector assembly and the detector shield are disposed concentrically around the patient. One embodiment for cardiac imaging, described in U.S. patent application Ser. No. 10/933,036, includes approximately 64 emission detector modules, each consisting of an array of individual elements or pixels. In this embodiment, detector shield provides a detector aperture arc having a radius of approximately 30 cm, and the detector assembly forms an arc with an inside radius of 40 cm. In this example, a patient field-of-view area with a diameter of approximately 50 cm fits within the field of view. The field of view may be defined by the area enclosed by the source mask and the detector shield, or other imaging components. The detector aperture arc and the detector assembly may be arranged in a true geometric arc with common arc centers on the longitudinal axis through the center of the field of view. Alternatively, either or both may be ovalized, or be arcuate with non-shared arc centers. For example, the arc centers may be positioned away from the longitudinal axis so as to increase the arc radii. It is also possible for any of the source, source aperture, detector aperture, or detector configurations to be non-arcuate. For example, either could be arranged as a one or more straight segments, or be partially arcuate and partially non-arcuate.

An apparatus according to an example of the present invention may further include an ergometer for physical activity of a patient, for example to stress the heart before imaging. An apparatus may further include an electrocardiogram, a cardiac defibrillator, and/or an intravenous infusion pump for administration of radiolabeled pharmaceuticals or other compounds.

In a further embodiment, a single photon emission computed tomography (SPECT) apparatus for producing multiple tomographic images of the type representing a three-dimensional distribution of a photon-emitting radioisotope comprises: a base including a patient support for supporting a patient such that a portion of the patient is located in a field of view, a longitudinal axis being defined through the field of view; a detector assembly adjacent to the field of view, the detector assembly extending at least partially about the field of view between a first end and a second end, the first and second ends being spaced apart so as to define an entry opening to the field of view, the detector assembly being operable to detect if a photon strikes the detector assembly; a collimating assembly including at least two spaced apart collimating vanes of photon-attenuating material, each of the vanes being disposed between the detector assembly and the field of view; a generally arcuate detector shield comprising a photon-blocking member disposed between the field of view and the detector assembly, the blocking member having a plurality of detector apertures (such as slots) defined therethrough at intervals along the member for passage of photons aligned with the aperture slots, lines of response for the detector assembly being defined from the detector assembly through the detector apertures; and a displacement actuator operable to move the photon-blocking member relative to the detector assembly such that the aperture slots are displaced relative to the detector assembly and the lines of response are swept across at least a portion of the field of view. The apparatus further comprises a plurality of x-ray sources disposed adjacent the field of view. The detector assembly may be used for both x-ray imaging and gamma emission imaging, for example forming a gamma emission image when the x-ray source is inactive. Alternatively, the detector assembly may be shielded from x-rays from the x-ray sources, the x-rays having path directions not coincident with the detector fields of view, and separate x-ray detectors provided. The x-ray detectors, and optional associated x-ray shields, may act to block the x-rays reaching the detector assembly. The detector assembly may comprise a gamma camera or other emission detector.

Source and/or detector apertures may have adjustable dimensions, for example comprising slots having an adjustable width. This allows adjustment in the sensitivity and resolution of imaging.

Figure 10:
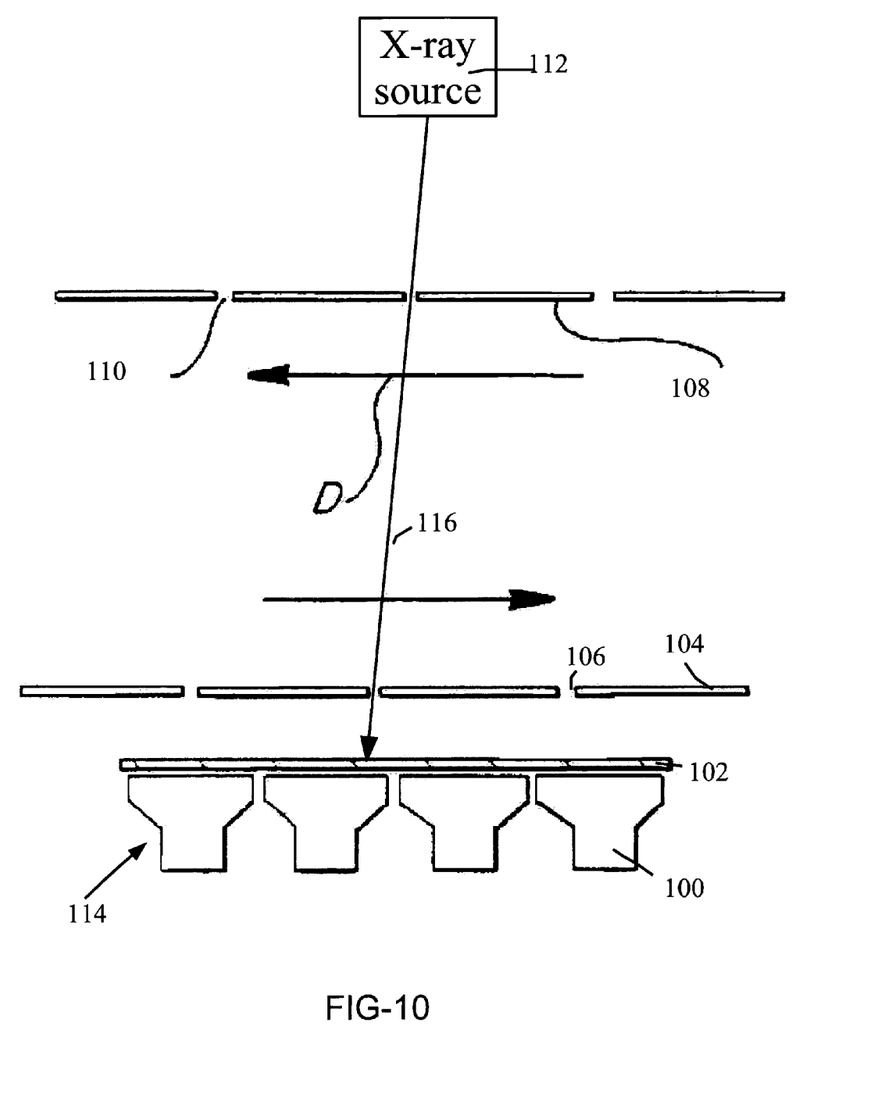
FIG. 10 illustrates a flat arrangement of detectors.

Even though examples show curved arrangement of detectors and source apertures, there is nothing about this design that mandates the detectors be curved. The same principles can be used with flat detectors. In such examples, the x-ray sources are arranged in a flat line and the source apertures are on a flat sheet (i.e., in a linear or quasilinear arrangement). FIG. 10 illustrates an apparatus comprising a detector assembly 114, in this example comprising scintillator 102 and photodetectors 100, detector apertures 106 in detector shield 104, x-ray source 112, and source aperture 110 in source mask 108. An x-ray beam 116 is collimated at a detector aperture and a source aperture, and falls on the detector assembly. The x-ray beam may be narrow, for example less than approximately 5 mm in width, for example in the range of approximately 1 mm to approximately 1.5 mm, and substantially non-divergent. The translation of source apertures, detector apertures, and (optionally) the x-ray sources can be coordinated so that the detectors are continuously capable of detecting the x-ray beam. More than one x-ray source may be used, and the x-ray source(s) may be pulsed. If the beam is not pulsed, continuous detection of the x-ray beam is possible during translation of the apertures. The arrows (D) indicate possible example directions of motion of source and detector apertures, though other motions are possible. Translation mechanisms, such as actuators, and other features are described in U.S. Pat. No. 6,525,320 to Juni, incorporated herein by reference.

Various examples described herein have described the transmitted radiation as x-rays and emission as gamma rays. However, in other examples of the present invention, the transmitted radiation and/or emission may be other types.

Patents, patent applications, or publications mentioned in this specification are incorporated herein by reference to the same extent as if each individual document was specifically and individually indicated to be incorporated by reference. In particular, U.S. U.S. Prov. Pat. App. Ser. Nos. 60/607,319, filed Sep. 3, 2004, and 60/652,424, filed Feb. 11, 2005, and U.S. patent application Ser. No. 10/933,036, are incorporated herein by reference in their entirety.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

I claim:

1. An apparatus for characterizing an emission from a field of view and an x-ray transmissivity of the field of view, the apparatus comprising:
   an x-ray source located adjacent to the field of view, the x-ray source providing x-rays;
   a source mask located between the x-ray source and the field of view, the source mask having a source aperture through which the x-rays pass, the x-rays having a path direction through the field of view;
   an emission detector located adjacent to the field of view, the emission detector detecting the emission from the field of view; and an x-ray detector located between the emission detector and the field of view so as to receive the x-ray beam after the x-ray beam passes through the field of view,
wherein the emission detector is shielded from the x-rays, the emission detector providing an emission signal correlated with the emissions from the field of view,
the x-ray detector providing an x-ray detector signal correlated with the x-ray transmissivity of the field of view for the path direction,
the apparatus further comprising an x-ray shield having a plurality of shield apertures therethrough,
the shield apertures being positioned so as to allow emission from the field of view to reach the emission detector, the x-ray shield preventing x-rays from reaching the emission detector.

2. The apparatus of claim 1, further comprising an actuator operable to move the source aperture relative to the x-ray source, so as to provide a change in the path direction through the field of view,
the x-ray detector moving in response to the change in the path direction so that the x-ray detector continues to receive the x-rays,
the emission detector remaining shielded from the x-rays as the path direction is changed.

3. The apparatus of claim 2, wherein the x-ray detector is mounted on an x-ray shield, the x-ray detector and x-ray shield moving together in response to the change in the path direction.

4. The apparatus of claim 1, wherein the emission detector is a gamma detector, the emission being gamma emission from the field of view.

5. The apparatus of claim 4, wherein the apparatus provides a gamma emission image of the field of view using a first signal from the emission detector,
the apparatus further providing an x-ray transmission image of the field of view using a second signal from the x-ray detector.

6. An apparatus for characterizing an emission from a field of view and an x-ray transmissivity of the field of view, the apparatus comprising:
an x-ray source located adjacent to the field of view, the x-ray source providing x-rays;
a source mask located between the x-ray source and the field of view, the source mask having a source aperture through which the x-rays pass, the x-rays having a path direction through the field of view;
an emission detector located adjacent to the field of view, the emission detector detecting the emission from the field of view; and
an x-ray detector located between the emission detector and the field of view so as to receive the x-ray beam after the x-ray beam passes through the field of view,
wherein the emission detector is shielded from the x-rays, the emission detector providing an emission signal correlated with the emissions from the field of view,
the x-ray detector providing an x-ray detector signal correlated with the x-ray transmissivity of the field of view for the path direction,
wherein the x-ray source is pulsed between an on state and an off state, so as to provide x-ray pulses having a pulse duration, the pulses separated by a pulse interval during which the x-ray source is in the off state, the x-ray source having a duty cycle equal to the pulse duration divided by the pulse interval,
the duty cycle being selected so that emission data and x-ray data are collected over a substantially concurrent time period,
wherein the pulse duration is between approximately 0.01 milliseconds and approximately 200 milliseconds,
the pulse interval being at least 10 times longer than the pulse length.

7. The apparatus of claim 6
the pulse interval being at least 100 times longer than the pulse length.

8. The apparatus of claim 1, wherein the source mask includes a plurality of source apertures, providing x-rays having a plurality of path directions through the field of view,
the apparatus further including an actuator operable to move the source mask relative to the x-ray source, so as to modify the plurality of path directions through the field of view.

9. The apparatus of claim 8, the apparatus further comprising a plurality of x-ray detectors positioned to detect at least part of the x-rays having the plurality of path directions.

10. The apparatus of claim 8, further comprising a plurality of x-ray sources arranged substantially in a first arc, and wherein the plurality of source apertures are arranged substantially in a second arc.

11. An apparatus for characterizing a field of view, the apparatus comprising:
an x-ray source;
a source mask located between the x-ray source and the field of view, the source mask having a source aperture;
a detector, located adjacent the field of view;
a detector shield located between the field of view and the detector, the detector shield having a detector aperture; and
an actuator, operable to move the source mask and the detector shield relative to the x-ray source, so as to adjust a path direction of an x-ray beam passing through the source aperture, the field of view, and the detector aperture,
wherein the source aperture and detector aperture are sized so that the x-ray beam is substantially non-divergent through the field of view.

12. The apparatus of claim 11, wherein the apparatus comprises a plurality of x-ray sources,
the source mask has a plurality of source apertures,
the detector shield has a plurality of detector apertures,
the actuator being operable to move the source mask and the detector shield relative to the plurality of x-ray sources, so as to adjust path directions of a plurality of substantially non-divergent x-ray beams through the field of view.

13. The apparatus of claim 12, wherein:
the plurality of x-ray sources is arranged substantially in a first arc,
the plurality of source apertures is arranged substantially in a second arc, and
the plurality of detector apertures is arranged in a third arc.

14. The apparatus of claim 12, wherein movements of the x-ray source, the source aperture, and detector aperture are coordinated so that the x-ray beam is continuously capable of being received by the detector.

15. The apparatus of claim 11, wherein the detector is part of an arcuate detector assembly.

16. The apparatus of claim 11, wherein the x-ray source is pulsed between an on state and an off state, so as to provide x-ray pulses having a pulse duration, the pulses separated by a pulse interval during which the x-ray source is in the off state, the x-ray source having a duty cycle, wherein the apparatus provides an x-ray image of the field of view using the detector signal obtained when the x-ray source is in the on state, the apparatus further providing an emission image of the field of view using the detector signal obtained when the x-ray source is in the off state, the duty cycle being selectable so that emission data and x-ray data are collected over a substantially concurrent time period.

17. The apparatus of claim 16, wherein the emission image is an image of gamma emission from the field of view.

18. The apparatus of claim 16, wherein the pulse duration is between approximately 0.01 milliseconds and approximately 200 milliseconds.

19. The apparatus of claim 16, wherein the pulse duration is between approximately 0.5 milliseconds and 20 milliseconds.

20. The apparatus of claim 16, wherein the pulse interval is at least 10 times longer than the pulse length.

21. An apparatus for providing an emission image and an x-ray image of a field of view, the apparatus comprising:
   an x-ray source, pulsed between an on state and an off state, so as to provide x-ray pulses having a pulse duration, the pulses separated by a pulse interval during which the x-ray source is in the off state, the x-ray source having a duty cycle;
   an emission detector, providing an emission detector signal in response to emissions from the field of view;
   an x-ray detector, providing an x-ray detector signal in response to x-rays passing through the field of view and incident on the x-ray detector; and
   electronic circuitry operable to:
      form an x-ray image of the field of view from the x-ray detector signal, and
      form an emission image of the field of view from the emission detector signal, the emission image being an image of the emissions from the field of view,
   the duty cycle being selectable so that emission data and x-ray data are collected over a substantially concurrent time period,
   the pulse duration being between approximately 0.01 milliseconds and approximately 200 milliseconds, and
   the pulse interval being at least 10 times longer than the pulse length.

22. The apparatus of claim 21, wherein the emission detector and x-ray detector are both provided by the same detector assembly, the detector assembly providing a detector signal,
   the x-ray detector signal being the detector signal when the x-ray source is in the on state,
   the emission detector signal being the detector signal when the x-ray source is in the off state.

23. The apparatus of claim 21, wherein the pulse interval is over one hundred times greater than the pulse length.

24. The apparatus of claim 21, wherein the emission is gamma emission.

* * * * *

UNITED STATES PATENT AND TRADEMARK OFFICE
CERTIFICATE OF CORRECTION

| | |
|---|---|
| PATENT NO. | : 7,310,407 B2 |
| APPLICATION NO. | : 11/218936 |
| DATED | : December 18, 2007 |
| INVENTOR(S) | : J. Juni |

It is certified that error appears in the above-identified patent and that said Letters Patent is hereby corrected as shown below:

Column 5, line 18, replace "may includes" with --may include--

Column 5, line 48, replace "be effectively be" with --be effectively--

Column 6, line 17, replace "or more a detector" with --or more detector--

Column 6, line 36, replace "detector can part" with --detector can be part--

Column 6, line 42, replace "a arcuate" with --an arcuate--

Column 10, line 57, replace "40A-4D" with --40A-40D--

Column 15, line 25, replace "and intravenous" with --an intravenous--

Signed and Sealed this

Third Day of June, 2008

JON W. DUDAS
*Director of the United States Patent and Trademark Office*